US012762696B2

(12) United States Patent
Ditt et al.

(10) Patent No.: US 12,762,696 B2
(45) Date of Patent: Oct. 13, 2026

(54) METHOD FOR PROVIDING A VIRTUAL, NONCONTRAST IMAGE DATASET

(71) Applicant: Siemens Healthineers AG, Forchheim (DE)

(72) Inventors: Hendrik Ditt, Neustadt an der Aisch (DE); Oliver Taubmann, Weilersbach (DE)

(73) Assignee: Siemens Healthineers AG, Forchheim (DE)

( * ) Notice: Subject to any disclaimer, the term of this patent is extended or adjusted under 35 U.S.C. 154(b) by 367 days.

(21) Appl. No.: 18/496,389

(22) Filed: Oct. 27, 2023

(65) Prior Publication Data

US 2024/0144479 A1 May 2, 2024

(30) Foreign Application Priority Data

Oct. 31, 2022 (EP) .................................... 22204679

(51) Int. Cl.
*G06T 7/00* (2017.01)
*A61B 6/00* (2024.01)
(Continued)

(52) U.S. Cl.
CPC ............ *G06T 7/0012* (2013.01); *A61B 6/504* (2013.01); *G06T 7/20* (2013.01); *G06T 2207/10081* (2013.01); *G06T 2207/30016* (2013.01)

(58) Field of Classification Search
CPC ..................... G06T 7/0012; G06T 7/20; G06T 2207/10081; G06T 2207/30016;
(Continued)

(56) References Cited

U.S. PATENT DOCUMENTS 6,248,074 B1 6/2001 Ohno et al.
2014/0343358 A1 11/2014 Hameed et al.
(Continued)

OTHER PUBLICATIONS

Ronneberger et al.: "U-Net: Convolutional Networks for Biomedical Image Segmentation"; Medical Image Computing and Computer-Assisted Intervention—MICCAI 2015 : 18th International Conference, Munich, Germany, Oct. 5-9, 2015; Oct. 9, 2015.
(Continued)

*Primary Examiner* — Siamak Harandi
(74) *Attorney, Agent, or Firm* — Harness, Dickey & Pierce, P.L.C.

(57) ABSTRACT

One or more example embodiments of the present invention relates to a method for providing a virtual, noncontrast image dataset of a patient comprising providing a multiphase CT angiography image dataset of the patient, the multiphase CT angiography image dataset comprising at least three CT image datasets that map an imaging area of the patient at three different points in time relative to an administration of a contrast agent; forming a minimum intensity image dataset of the imaging area based on the at least three CT image datasets, an image value of an image point of the minimum intensity image dataset is in each case based on a minimum value from among image values of the image point, locally corresponding in the imaging area, in the at least three CT image datasets; and outputting of the virtual, noncontrast image dataset based on the minimum intensity image dataset.

19 Claims, 5 Drawing Sheets

(51) Int. Cl.
*A61B 6/50* (2024.01)
*G06T 7/20* (2017.01)

(58) Field of Classification Search
CPC ..................... G06T 7/0014; G06T 7/97; G06T 2207/30101; A61B 6/504; A61B 6/481; A61B 6/484; A61B 6/507; A61B 6/5205; A61B 6/5264; A61B 6/032; A61B 6/035; A61B 6/501; A61B 6/5229; G16H 30/20
See application file for complete search history.

(56) References Cited

U.S. PATENT DOCUMENTS

| | | | |
|---|---|---|---|
| 2017/0265829 A1 | 9/2017 | Adam et al. | |
| 2021/0236080 A1* | 8/2021 | Herrmann .............. | G16H 50/70 |
| 2022/0087631 A1 | 3/2022 | D'Esterre et al. | |

OTHER PUBLICATIONS

Shen W., Ruje L. et al.:"Learning Residual Images for Face Attribute Manipulation" (https://doi.org/10.48550/arxiv.1612.05363).
Zhang Li, Chefd'hotel C. et al.:"Group-wise motion correction of brain perfusion images," (2010 IEEE International Symposium on Biomedical Imaging: From Nano to Macro, 2010, pp. 832-835, doi: 10.1109/ISBI.2010.5490115.).

* cited by examiner

METHOD FOR PROVIDING A VIRTUAL, NONCONTRAST IMAGE DATASET

CROSS-REFERENCE TO RELATED APPLICATION(S)

The present application claims priority under 35 U.S.C. § 119 to European Patent Application No. 22204679.9, filed Oct. 31, 2022, the entire contents of which are incorporated herein by reference.

FIELD

One or more example embodiments of the present invention relates to a method for providing a virtual, noncontrast image dataset of a patient on the basis of a multiphase CT angiography image dataset (mCTA image dataset) of the patient, for example, at least three CT image datasets that map an imaging area of the patient at three different points in time relative to an administration of contrast agent. One or more example embodiments of the present invention further relates to an associated apparatus for providing a virtual, noncontrast image dataset of a patient, a computed tomography device, a computer program product and a computer-readable storage medium.

RELATED ART

In the event of an acute stroke it is necessary to perform multiple examinations in order to determine the cause and severity of the stroke. Generally a computed tomography (CT) examination is initially performed without the administration of contrast agent, in order to find out whether a hemorrhage is present in the patient, and in order to look for early signs of a stroke (for example determination of hyperdense MCA signs, of the “Alberta Stroke Program Early CT Score”, ASPECTS for short, etc.). If no hemorrhage can be found, a CT angiography (CTA) is performed, followed by a perfusion CT examination (CTP). During the CTP the area of interest is repeatedly scanned over a certain period of time at multiple points in time, for example every 1.5 seconds over a period of 40 seconds and thus a time-resolved 3D dataset is generated, which shows the inflow and outflow of the contrast agent in the vessels of the area of interest, in particular the brain. The clot may be localized in the CTA, while the CTP can provide information about the severity of the stroke and answer the question as to whether there is still an area of viable cells (penumbra) adjoining a central zone of necrosis that could be saved by treatment. In some hospitals this perfusion CT examination is replaced by a multiphase CTA (mCTA). In an mCTA acquisition, after the first CTA from the aortic arch to the crown, just two further scans are generally performed, in which only the brain is scanned. These three scans provide a significantly lower time resolution than a CTP, but more information about the distribution of contrast agent in the brain than a CTA alone.

The possibility exists of using the mCTA data quantitatively and of creating results images therefrom, similar to those used in the analysis of CT perfusion scans. This comprises what are known as “perfusion maps”, for example CBF (cerebral blood flow), which indicates what volume of blood (ml) is flowing per mass of tissue (g) per time (min), CBV (cerebral blood volume), which indicates what volume of blood (ml) is to be found per mass of tissue (g) or TTP (time-to-peak, also referred to as time to maximum hyperdensity), which indicates how much time a contrast agent bolus needs until it is maximally concentrated in a particular tissue region.

Examinations using mCTA are not restricted to stroke patients. In addition, there can also be other applications, for example for a tumor assessment.

However, for the creation of these perfusion image datasets, in other words the perfusion maps, a basic image dataset of the diagnostically relevant area is necessary, which corresponds to a noncontrast CT image dataset, i.e. a CT image dataset without the presence of contrast agent. In the CTP this does not generally represent a problem, since here the scan already starts when the contrast agent has not yet reached the area of interest.

As previously described, a CT image dataset without a prior administration of contrast agent, also referred to below as a native, noncontrast CT image dataset, is frequently additionally available since this frequently occurs at the start of the examinations of a stroke patient. However, this is generally acquired with other scanning parameters such as the subsequent mCTA scans. Thus this first scan, in other words the native, noncontrast CT image dataset, is normally performed with a higher X-ray tube voltage, for example at 120 kVp, in order to achieve an optimum image quality for soft tissue. In contrast to this, CTA scans are generally performed with a lower X-ray tube voltage relative to this, for example 80-100 kVp, in order to attain a better contrast agent contrast for the visualization of the vascular system. Furthermore, special image filters are frequently applied to native, noncontrast CT image datasets, whereas other filters are generally applied to CTA image datasets.

SUMMARY

Despite these differences the native, noncontrast image dataset is generally at present used as the basic image dataset for calculating perfusion maps on the basis of mCTA image datasets. However, because of the different scanning parameters this results in problems and artifacts.

One or more example embodiments of the present invention provides a method which allows an improved noncontrast image dataset of a patient for example to be provided for optional, subsequent processing of the patient’s multiphase CT angiography image dataset (mCTA image dataset). Likewise one or more example embodiments of the present invention provides an associated apparatus, a computed tomography device, a computer program product and a computer-readable storage medium.

The is achieved by the method and the apparatuses that are described in the independent claims. Embodiments that are advantageous and in themselves inventive form the subject matter of the subclaims and of the subsequent description.

BRIEF DESCRIPTION OF THE DRAWINGS

Example embodiments are described below with reference to the appended figures. The representation in the figures is schematic, greatly simplified and not necessarily true to scale. In the drawing.

DETAILED DESCRIPTION

Figure 1:
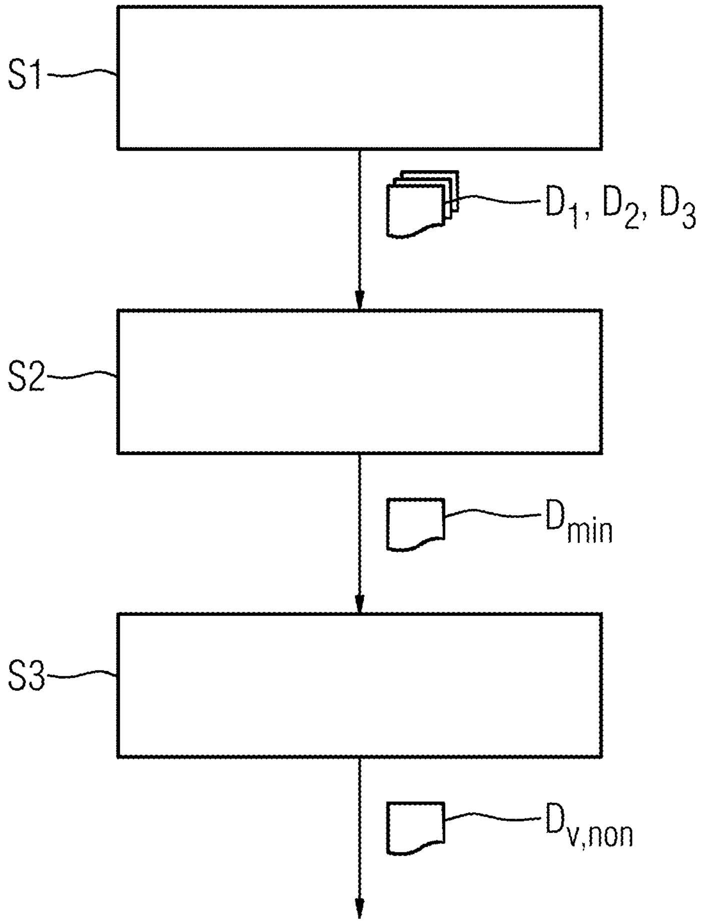
FIG. 1 shows a method for providing a virtual, noncontrast image dataset of a patient according to one or more example embodiments.

One or more example embodiments of the present invention relates to a method for providing a virtual, noncontrast CT image dataset of a patient comprising the steps provision of a multiphase CT angiography image dataset of the patient comprising at least three CT image datasets that map an imaging area of the patient at three different points in time relative to an administration of contrast agent, via an interface, formation of a minimum intensity image dataset of the imaging area on the basis of the at least three CT image datasets, wherein the image value of an image point of the minimum intensity image dataset is in each case based on the minimum value from among the image values of the image points, locally corresponding in the imaging area, in the at least three CT image datasets, via a computing unit, output of the virtual, noncontrast CT image dataset on the basis of the minimum intensity image dataset via a further interface.

A virtual, noncontrast CT image dataset corresponds to an image dataset that maps the imaging area of the patient without the image values being influenced by a contrast agent. The virtual, noncontrast CT image dataset is referred to as virtual, in contrast to the native, noncontrast CT image dataset, since it is not based on the acquisition of measured data that has been captured without the administration of contrast agent, but is generated subsequently via a computing unit on the basis of measured data that has been captured with the administration of contrast agent.

The CT image datasets provided and determined in connection with the method, comprising the minimum intensity image dataset, can in particular in each case be a three-dimensional image dataset (3D image dataset). A 3D image dataset permits a three-dimensional, in particular spatially three-dimensional, representation of the imaging area of the patient. A 3D image dataset can also be represented as a plurality of slice image datasets. A slice image dataset in each case comprises a slice of the 3D image dataset at a position along a singular axis. A slice image dataset then in each case permits a two-dimensional, in particular spatially two-dimensional, representation of the respective slice.

A 3D image dataset such as this advantageously comprises multiple voxels, in particular image points. In this case each voxel can advantageously in each case have an image value, in particular a CT image value in HU ("Hounsfield Units") or an intensity value analogous thereto. Analogously thereto, a slice image dataset can comprise multiple pixels, in particular image points. In this case each pixel can advantageously in each case have an image value, in particular a CT image value in HU ("Hounsfield Units") or an intensity value analogous thereto. The at least three CT image datasets can in particular correspond in respect of their image resolution.

The patient can be an animal patient and/or a human patient. Further, the imaging area of the patient can comprise an anatomical and/or spatial area of the patient, which comprises a predetermined tissue area and/or a spatial area necessary for a diagnosis. The imaging area can in this case comprise a body area, for example the head or the thorax.

The provision of the at least three CT image datasets of the mCTA image dataset can for example comprise a capture and/or readout of a computer-readable data memory and/or a receipt from a memory unit. Further, the inventive method can also comprise an acquisition of the at least three CT image datasets of the mCTA image dataset via a CT device, which can then be provided for the further steps of the method. The output can for example comprise an output to a downstream processing unit which further processes the provided virtual, noncontrast CT image dataset, for example generates perfusion maps. The output can also comprise an output to a display unit, for example comprising a monitor, which permits the display of the image dataset for a user.

The at least three CT image datasets, just as the virtual, noncontrast CT image dataset and the minimum intensity image dataset, all map at least the imaging area of the patient. The imaging area in particular comprises the area of the patient that is to be evaluated in a downstream diagnostic study via the image information obtained from the mCTA image dataset. However, the acquisition areas of the at least three CT image datasets, for which measured data is to be acquired, may be, but do not have to be, different, providing they in each case comprise the imaging area. Thus for example the acquisition area of the first of the at least three CT image datasets in time can comprise another, in particular more extensive, acquisition area than the second and/or third of the at least three CT image datasets in time. The imaging area can correspond to the smallest of the acquisition areas, in respect of the mapped spatial extent, of the at least three CT image datasets. However, it may also be just a section thereof.

For example, the imaging area in particular comprises the brain of a patient. A virtual, noncontrast CT image dataset can advantageously be provided for further processing of the mCTA image dataset, for example for perfusion image datasets of the brain. Thus on the basis of a virtual, noncontrast CT image dataset such as this an improved stroke diagnostic investigation can be enabled, if the virtual, noncontrast CT image dataset is employed in the provision of perfusion image datasets. For example, the acquisition area of the first CT image dataset can comprise at least the patient from the aortic arch to the crown, and the acquisition area of the second CT image dataset and/or the acquisition area of the third CT image dataset can at least map the patient from the base of the skull to the crown. For example, the imaging area corresponds to the acquisition area of the second and/or third CT image dataset or at least one section thereof. In other forms of embodiment the imaging area can also map another body area of the patient.

Imaging examinations using contrast agent, for example contrast agent administered to the patient intravenously on the basis of iodine, are performed in order to improve the visibility of blood vessels, organ tissue, tumorous structures or hemorrhages. Further diagnostically relevant information can be obtained about the progress over time of the distribution of contrast agent. The at least three CT image datasets map the imaging area of the patient at three different points in time relative to, i.e. in particular subsequent in time to, an administration of contrast agent. The at least three CT image datasets therefore in each case map the status of the distribution of the contrast agent in the patient at different points in time after an administration of contrast agent.

For example, the first in time of the at least three CT image datasets of the mCTA image dataset maps the status of the distribution of the contrast agent in the patient at the highpoint of an arterial phase. For example, the second in time of the at least three CT image datasets maps the status of the distribution of the contrast agent in the patient at the highpoint of the venous phase. For example, the third in time of the at least three CT image datasets maps the status of the distribution of the contrast agent in the patient in a late venous phase. Different phases can also be selected for different applications.

The respective point in time of the measured data acquisition for the at least three CT image datasets can be based on empirical values or for example can be ascertained at least in part using bolus tracking methods or test bolus methods.

The relative time interval between the first CT image dataset in time and the second CT image dataset of the at least three CT image datasets or of the relative time interval between the second CT image dataset in time and the third CT image dataset of the at least three CT image datasets is in preferred embodiments at least 5 s. For example, the data acquisition of the second CT image dataset starts 7, 8 or 10 s after the start of the first CT image dataset, for example the data acquisition of the third CT image dataset starts between 7, 8 or 10 s after the start of the second CT image dataset. For the mCTA in the context of a diagnostic investigation in connection with a stroke a time interval of 7-10 s is particularly advantageous. For other applications this may vary. In particular, the time delay between the respective starts of the data acquisition is selected such that the CT image datasets are suitable for a subsequent diagnostic investigation. In this case the relative time interval between the first CT image dataset in time and the second CT image dataset or the relative time interval between the second CT image dataset in time and the third CT image dataset of the at least three CT image datasets may be different.

The minimum intensity image dataset maps at least the imaging area. Therefore in respect of the mapping it can also correspond to the smallest of the acquisition areas, in respect of the spatial extent, of the at least three CT image datasets. However, it can also map just a section thereof.

The image values of the minimum intensity image dataset are each based on the minimum value from among the image values of the image points, locally corresponding in the imaging area, in the at least three CT image datasets. This means the image value of an image point of the minimum intensity image dataset is in each case based on the image value of the locally corresponding image point in the imaging area of that one of the at least three CT image datasets that has the minimum image value. In particular, they can correspond thereto. However, they can also each be based on this minimum value and adjusted. For the formation of the minimum intensity image dataset a preliminary image dataset can for example be formed, whose image points, i.e. voxels or pixels, are provided with the respective image value of one of the at least three CT image datasets that is minimal. In this case, locally corresponding means that locally corresponding image points in the at least three CT image datasets and accordingly also in the minimum intensity image dataset each map the same image area of the patient. This procedure can therefore be understood as a minimum intensity projection based on the mCTA image dataset along the time axis. The minimum value in a CT image dataset corresponds, due to the normal representation of a CT image dataset, in particular to the value that corresponds to the highest transmission of X-ray radiation, i.e. the least absorption.

The consideration behind the inventive procedure is accordingly as follows: since the at least three CT image datasets represent the imaging area in each case at different points in time relative to the administration of contrast agent, the assumption is that for each mapped area or tissue type in the imaging area a mapping is present in one of the three CT image datasets in which this is not influenced by contrast agent, so that the image area of the CT image dataset for which this applies can be used for this area as a noncontrast image. It can in this case then further be assumed that the respective minimum image value for a corresponding image point or voxel in the at least three CT image datasets corresponds to the one that is not influenced by contrast agent, since the contrast agent would result in an increase in the image value relative to an initial value.

As applied to the example of a stroke patient this means: in healthy brain tissue the contrast agent reaches the tissue and vessels very early, so that the first in time of the at least three CT image datasets has an influence due to contrast agent in the parenchyma of the brain. However, no more contrast agent can be present in these parts of the brain in the last in time of the at least three CT image datasets, since this will already be washed out. The penumbra around the core area of the infarction will be amplified in image datasets, with a delay relative to healthy tissue, via the contrast agent. This will consequently be present uninfluenced in the first in time of the at least three CT image datasets. In the brain tissue in question of the core area of the infarction the mapping will always be unimpaired by contrast agent, since this does not reach that far. Consequently at least one mapping not influenced by contrast agent is available in each case for each tissue area, on which a virtual, noncontrast CT image dataset can be based which then for example can be provided as a basic image for optional further processing of the mCTA image dataset.

A noncontrast CT image dataset can advantageously be provided via the inventive method and is based on measured data that corresponds to the acquisition conditions that were used for the at least three CT image datasets. A diagnostic investigation and further processing of the image datasets on the basis of the improved noncontrast image dataset can then advantageously take place and thus an improved quality can be achieved. Where appropriate a further dose application can advantageously be dispensed with, in order to generate a noncontrast CT image dataset from the patient that corresponds to the mCTA image dataset and is based on measured data with the same scanning parameters as the mCTA image dataset.

In accordance with an advantageous embodiment variant the method additionally comprises the step:

performance of a motion correction of the at least three CT image datasets, as a result of which motion-corrected CT image datasets are provided, and wherein the minimum intensity image dataset is formed on the basis of the motion-corrected CT image datasets.

The proposed method can in particular be used particularly advantageously whenever the at least three CT image datasets map the patient or the imaging area in an unchanged position and unchanged status (apart from the distribution of contrast agent). Because of movements of the mapped structures between the individual acquisitions, interfering motion artifacts can occur in the minimum intensity image dataset. One consequence of these movements may be that the resulting virtual, noncontrast CT image dataset cannot be used for subsequent further processing and a diagnosis based thereon. A motion correction can advantageously take account of movements of the patient between the measured data acquisition for the at least three CT image datasets and reduce their effect, and thus an improved minimum intensity image dataset can be provided.

For a motion correction, as can be employed in connection with the method, there are different options that are known to the person skilled in the art from the prior art. The aim is in particular a registration and transformation of the structures of the at least three CT image datasets to one another, so that in an advantageous manner a minimum intensity image dataset based on the corrected at least three CT image datasets can be calculated. In particular, a known rigid registration can be used. For example, a method as described in Zhang L, Chefd'hotel C, Bousquet G "Group-wise motion correction of brain perfusion images," (2010 IEEE International Symposium on Biomedical Imaging: From Nano to Macro, 2010, pp. 832-835, doi: 10.1109/ISBI.2010.5490115.) can also be used.

However, other methods can also be employed, with the result that artifacts in the minimum intensity image dataset caused by movement of the patient are at least reduced.

In accordance with an advantageous embodiment variant of the method, the following steps are also included:

provision of a native, noncontrast CT image dataset that maps the imaging area of the patient without administration of contrast agent, and correction of the minimum intensity image dataset using the native, noncontrast CT image dataset, as a result of which a corrected minimum intensity image dataset is provided, and wherein the virtual, noncontrast image dataset that is output is based on the corrected minimum intensity image dataset.

The native, noncontrast CT image dataset is in particular acquired with scanning parameters which differ from the scanning parameters of the at least three CT image datasets of the multiphase CT angiography image dataset. This relates in particular to operating parameters of the X-ray source, such as an X-ray tube voltage and/or an X-ray tube current. The native, noncontrast CT image dataset can for example be performed with a higher X-ray tube voltage than the at least three CT image datasets, in order to achieve an optimum image quality for soft tissue. The native, noncontrast CT image dataset is generally acquired prior in time to the at least three CT image datasets and maps the imaging area of the patient before the administration of contrast agent and without influence therefrom.

As already described previously, the direct use of the native, noncontrast CT image dataset is, because of different scanning parameters, suitable only to a limited extent for further processing of the mCTA image dataset for example to form perfusion maps. However, this can advantageously be employed to correct the minimum intensity image dataset, in order to provide an improved virtual, noncontrast CT image dataset. Thus for example noisy regions in the at least three CT image datasets of the mCTA image dataset may, because of the calculation of the minimum during the creation of the minimum intensity image dataset, cause a distortion leading to a local underestimation of the tissue density. Such underestimated regions in the virtual, noncontrast CT image dataset may (erroneously) result in a locally higher contrast agent absorption during further processing of the image datasets to form perfusion maps on the basis of the virtual, noncontrast CT image dataset. Based on a comparison of the native, noncontrast CT image dataset and minimum intensity image dataset a correction can advantageously be performed. For example, a comparison of a contrast between structures or image areas present and surrounding structures or areas can be used to perform a correction based thereon. This can in particular happen whenever the comparison of the relationships in the native, noncontrast CT image dataset and in the minimum intensity image dataset shows an unexpectedly large deviation. If a relationship or a contrast in both image datasets is similar or within a specified expectancy range, there is a greater probability that no artifact is present here but that the image values are actually present as such and the structures are correctly reproduced.

In this case too, a motion correction can be performed prior to a comparison in order to take account of possible movements of the patient between the acquisition of the native, noncontrast CT image dataset and the at least three CT image datasets underlying the minimum intensity image dataset.

In advantageous embodiments of this method variant the step of correction means that for the correction a prior determination is made of image areas in the minimum intensity image dataset that exceed a particular noise level value or that fall below a particular intensity value, and on the basis of a comparison of these determined image areas with locally corresponding image areas in the native, noncontrast CT image dataset at least one correction value for the determined image areas is ascertained in the minimum intensity image dataset.

Likewise it is possible that, for the correction, image areas in at least one of the at least three CT image datasets are ascertained that exceed a particular noise level value or that fall below a particular intensity value, and on the basis of a comparison between image areas in the minimum intensity image dataset in each case locally corresponding thereto and in the native, noncontrast CT image dataset at least one correction value for the determined image areas in the minimum intensity image dataset is ascertained.

Based on the noise level value or a low intensity value, image areas can be ascertained which with a higher probability result in a distorted calculation of the minimum intensity image dataset. After identification of these areas with an increased probability a distorted image value determination for the minimum intensity image dataset, a check and where appropriate a correction can advantageously take place.

Alternatively to determining image areas on the basis of the minimum intensity image dataset or at least one of the at least three CT image datasets, the correction can also comprise determining image areas that are possibly to be corrected in a perfusion image dataset based on the uncorrected minimum intensity image dataset. This method variant then comprises, on the basis of the at least three CT image datasets of the multiphase CT angiography image dataset and the minimum intensity image dataset of the patient available on an uncorrected basis, creating a perfusion image dataset, identifying image areas of the perfusion image dataset with locally increased contrast agent absorption, and ascertaining at least one correction value on the basis of a comparison between image areas locally corresponding thereto in the minimum intensity image dataset and locally corresponding image areas in the native, noncontrast CT image dataset.

As described previously, noisy regions in the at least three CT image datasets of the mCTA image dataset can cause a distortion leading to a local underestimation of the tissue density due to the calculation of the minimum during the creation of the minimum intensity image dataset. Such underestimated regions in the preliminary uncorrected minimum intensity image dataset may (erroneously) result in a locally higher contrast agent absorption during further processing of the image datasets to form perfusion maps. Areas with locally higher contrast agent absorption in a perfusion image dataset therefore represent areas in which an incorrect determination of the values in the minimum intensity image dataset could be present with an increased probability. These are identified and are subject to a check and where appropriate a correction on the basis of a comparison with the native, noncontrast CT image dataset.

In the variants described previously the correction value can in particular be based on a ratio of the image values in the determined image areas of the minimum intensity image dataset or of the native, noncontrast CT image dataset to image values in an area surrounding the determined image areas of the minimum intensity image dataset or of the native, noncontrast CT image dataset. The comparison can in particular comprise comparing a contrast value between structures or image areas present to surrounding structures or areas. If a ratio in both image datasets is similar or within a range of expectation, the greater is the probability that no artifact is present here but that the image values are actually present as such. If the ratio differs significantly or lies outside expectations, the image values in the previously determined image areas of the minimum intensity image dataset are adjusted via at least one correction value, for example in a manner such that a ratio similar to or the same as the one in the native, noncontrast CT image dataset results therefrom or lies within the range of expectation. An alignment, as of when an adjustment should take place, for example of a range of expectation, and to what extent an adjustment has to take place, can for example be made using empirical values or series of measurements. For example, the measurement of phantoms can also be used for this.

One or more example embodiments of the present invention additionally relates to a method for providing a perfusion image dataset, wherein a multiphase CT angiography image dataset of the patient comprising at least three CT image datasets is provided, that map an imaging area of the patient at three different points in time relative to an administration of contrast agent, a virtual, noncontrast CT image dataset of the imaging areas is, as claimed in one of the preceding claims, provided on the basis of the at least three CT image datasets, and a perfusion image dataset is generated and provided on the basis of the at least three CT image datasets and the virtual, noncontrast CT image dataset.

In particular, on the basis of the mCTA image dataset and the advantageously created virtual, noncontrast CT image dataset so-called "perfusion maps" are provided, for example CBF (cerebral blood flow), which indicates what volume of blood (ml) is flowing per mass of tissue (g) per time (min), or CBV (cerebral blood volume), which indicates what volume of blood (ml) is to be found per mass of tissue (g) and/or on the basis thereof further parameters are derived. Methods for calculating the parameters are known to the person skilled in the art from the prior art and can also be applied in the same manner here. However, via the virtual, noncontrast CT image dataset an improved perfusion image dataset can advantageously be provided, which in particular may be less affected by artifacts. Thus image datasets and values of a higher quality can advantageously be provided, which allows an improved subsequent diagnosis.

One or more example embodiments of the present invention further relates to an apparatus for providing a virtual, noncontrast image dataset of a patient comprising

- a first interface, designed to provide at least one multiphase CT image dataset of the patient, comprising at least three CT image datasets, each of which maps an imaging area of the patient at three different points in time relative to an administration of contrast agent,
- a computing unit, designed to form a minimum intensity image dataset of the imaging area on the basis of the at least three CT image datasets, wherein the image value of an image point of the minimum intensity image dataset is in each case based on the minimum value from among the image values of the image points, locally corresponding in the imaging area, in the at least three CT image datasets, and
- a second interface, designed to output the virtual noncontrast image dataset on the basis of the minimum intensity image dataset.

An apparatus such as this for providing a virtual, noncontrast image dataset of a patient can in particular be designed to execute the previously described inventive methods for providing a virtual, noncontrast image dataset of a patient and aspects thereof. The apparatus can be designed to execute the methods and aspects thereof, in that the interfaces and the computing unit are designed to execute the corresponding method steps.

The apparatus can further be designed to generate and provide a perfusion image dataset on the basis of a provided multiphase CT angiography image dataset of the patient comprising at least three CT image datasets that map an imaging area of the patient at three different points in time relative to an administration of contrast agent, and on the basis of a virtual, noncontrast CT image dataset of the imaging area provided on the basis of the at least three CT image datasets as claimed in one of the preceding claims.

The apparatus or the computing unit may in particular be a computer, a microcontroller or an integrated circuit. Alternatively, it may in this case be a real or virtual network of computers (a technical term for a real network is "cluster", a technical term for a virtual network is "cloud"). The apparatus can also be designed as a virtual system that is executed on a real computer or a real or virtual network of computers (virtualization).

An interface can be a hardware or software interface (for example PCI bus, USB or firewire). A computing unit can have hardware elements or software elements, for example a microprocessor or what is known as an FPGA (the acronym stands for "Field Programmable Gate Array").

The interfaces can in particular comprise multiple subsidiary interfaces. In other words, the interfaces can also comprise a plurality of interfaces. The computing unit can in particular comprise multiple subsidiary computing units that execute different steps of the respective methods. In other words, the computing unit can also be understood as a plurality of computing units.

The apparatus can additionally also comprise a memory unit. A memory unit can be implemented as a nonpermanent working memory (Random Access Memory, RAM for short) or as a permanent mass memory (hard disk, USB stick, SD card, solid state disk).

The advantages of the proposed apparatus substantially correspond to the advantages of the proposed method for providing a virtual, noncontrast image dataset of a patient. Features, advantages or alternative forms of embodiment mentioned here can likewise also be transferred to the apparatus and vice versa.

One or more example embodiments of the present invention further relates to a computed tomography device having an apparatus for providing a virtual, noncontrast image dataset of a patient as described previously. A computed tomography device comprises at least one X-ray source and a detector arranged opposite thereto, which are arranged on a rotatable gantry. The computed tomography device is designed to capture a plurality of projection datasets from different projection angles during a relative rotary motion between an X-ray source and a patient arranged between the X-ray source and the detector. Based on the plurality of projection datasets, CT image datasets can in each case be reconstructed and provided for further processing. The computed tomography device is in particular designed to provide the at least three CT image datasets of the mCTA image dataset that map the imaging area of the patient at three different points in time relative to an administration of contrast agent.

In this case the computed tomography device is advantageously designed to execute one or more example embodiments of the proposed method for providing a virtual, noncontrast image dataset of a patient.

The advantages of the proposed computed tomography device substantially correspond to the advantages of the proposed method for providing a virtual, noncontrast image dataset of a patient. Features, advantages or alternative forms of embodiment mentioned here can likewise also be transferred to the apparatus and vice versa.

One or more example embodiments of the present invention further relates to a computer program product having a computer program which can be loaded directly into a memory of an apparatus for providing a virtual, noncontrast image dataset of a patient, with program sections in order to execute all steps of an inventive method for providing a virtual, noncontrast image dataset of a patient, if the program sections are executed by the apparatus.

A computer program product can be a computer program or can comprise a computer program. As a result, the inventive method can be executed in a rapid, identically repeatable and robust manner. The computer program product is configured so that it can execute the inventive method steps via the apparatus. The apparatus must in each case have the prerequisites, such as for example a corresponding working memory, a corresponding graphics card or a corresponding logic unit, so that the respective method steps can be executed efficiently. The computer program product is for example stored on a computer-readable medium or on a network or server, from where it can be loaded into a computing unit of the apparatus.

One or more example embodiments of the present invention further relates to a computer-readable storage medium, on which are stored program sections that can be read and executed by an apparatus for providing a virtual, noncontrast image dataset of a patient, in order to execute all steps of an inventive method for providing a virtual, noncontrast image dataset of a patient as described previously, if the program sections are executed by the apparatus.

Examples of a computer-readable storage medium are a DVD, a magnetic tape, a hard disk or a USB stick, on which is stored electronically readable control information, in particular software.

A largely software-based implementation has the advantage that apparatuses and computing units used hitherto can also easily be upgraded by a software update, in order to work in the inventive manner. A computer program product can where appropriate comprise, besides the computer program, additional elements such as for example documentation and/or additional components, as well as hardware components, such as for example hardware keys (dongles, etc.) for the use of the software.

Besides the previously described inventive method for providing a virtual, noncontrast CT image dataset it is alternatively also possible to generate such a virtual, noncontrast CT image dataset on the basis of the use of a trained function. Accordingly an apparatus could also be provided that is designed to execute a method such as that described below. The apparatus can be designed to execute the methods and aspects thereof, in that suitable interfaces and a computing unit are provided which are designed to execute the corresponding method steps.

A method such as this would then at least comprise provision, via an interface, of a multiphase CT angiography image dataset of the patient comprising at least three CT image datasets that map an imaging area of the patient at three different points in time relative to an administration of contrast agent, generation of a virtual, noncontrast CT image dataset by applying a trained function to the mCTA image dataset via a computing unit, wherein at least one parameter of the trained function is adjusted to a comparison between a virtual, noncontrast training image dataset and a noncontrast comparison image dataset, wherein the generated virtual, noncontrast training image dataset and the noncontrast comparison image dataset are linked to one another, and subsequent output, via a further interface, of the generated virtual, noncontrast CT image dataset.

An explanation of what may be comprised by a virtual, noncontrast training image dataset and a noncontrast comparison image dataset is given in greater detail below.

A trained function can preferably be implemented via an artificial intelligence system, i.e. by a machine learning method. An artificial intelligence system may refer to a system for the artificial generation of knowledge from experience. An artificial system learns from examples in a training phase and on termination of the training phase can make generalizations. The use of a system such as this can comprise a recognition of patterns and laws in the training data. After the training phase the optimized, i.e. trained, algorithm can derive a virtual, noncontrast CT image dataset, for example on the basis of a previously unknown mCTA image dataset. The artificial intelligence system may be an artificial neural network or may also be based on another machine learning method. In particular, after the training phase a determination can automatically be enabled of the virtual, noncontrast CT image dataset particularly reliably and efficiently in terms of time via a trained function on the basis of an artificial intelligence system.

A trained function in particular maps input data to output data. The output data may here in particular further depend on one or more parameters of the trained function. The one or more parameters of the trained function may be determined and/or adjusted by training. The determination and/or adjustment of the one or more parameters of the trained function can in particular be based on a pair consisting of training input data and comparison output data associated, i.e. linked, thereto, wherein the trained function is applied to the training input data for the generation of training output data. In particular, the determination and/or adjustment can be based on a comparison of the training output data and the training comparison data. In general a trainable function, i.e. a function with one or more as yet unadjusted parameters, is also referred to as a trained function.

Other terms for trained function are trained mapping rule, mapping rule with trained parameters, function with trained parameters, algorithm based on artificial intelligence, machine learning algorithm. An example of a trained function is an artificial neural network, wherein the edge weights of the artificial neural network correspond to the parameters of the trained function. In place of the term "neural network" the term "neural net" can also be used. In particular, a trained function may also be a deep artificial neural network (deep neural network). In the context of this alternative method a neural network in the form of what is known as a U-Net (see for example: Ronneberger O, Fischer P and Brox T. U-Net: Convolutional Networks for Biomedical Image Segmentation, http://arxiv.org/abs/1505.04597) may in particular also be employed. However, other architectures known from the prior art may also be used, in particular those based on a deep learning model with an encoder-decoder architecture.

The trained function can in particular be trained using backpropagation. Training output data can initially be determined by applying the trained function to training input data. It is then possible to determine a deviation between the training output data and the training comparison data by applying an error function to the training output data and the training comparison data. Furthermore, at least one parameter, in particular a weighting, of the trained function, in particular of the neural network, can be iteratively adjusted on the basis of a gradient of the error function in respect of the at least one parameter of the trained function. As a result, the deviation between the training output data and the training comparison data can advantageously be minimized during the training of the trained function.

The trained function, in particular the neural network, advantageously has an input layer and an output layer. In this case the input layer can be designed to receive input data. Furthermore, the output layer can be designed to provide output data. In this case the input layer and/or the output layer can each comprise multiple channels, in particular neurons.

The input data for the trained function can comprise at least the at least three CT image datasets of an mCTA image dataset of the patient. The output data can in particular comprise the virtual, noncontrast CT image dataset.

To train the trained function it is necessary to provide training data. The training data comprises the previously mentioned virtual, noncontrast training image dataset as training output data and the noncontrast comparison image dataset as training comparison data.

For the training the training input data is provided, which applies the trained function to the provided training input data, in order to obtain training output data, and finally parameters of the trained function are adjusted on the basis of a comparison of the training output data with training comparison data associated therewith. The training input data and the training comparison data are linked to one another. In particular, annotated training input data can be employed.

Training input data, via which training output data is determined by applying the trained function to the training input data in the training phase, and training comparison data can be generated or provided in different ways.

In an advantageously simple form the training input data can correspond to mCTA image datasets measured on the patient or with phantoms, wherein training comparison data can be provided as an additional noncontrast image dataset, which with the same scanning parameters as the measured mCTA image dataset was however captured without the influence of contrast agent. This represents an advantageously simple and direct training variant. However, this is disadvantageously accompanied by the need for additional measurements and thus effort, in particular in view of the fact that an extensive set of training data should be made available for the training. Particularly in the case of measurements on the patient this is also linked to an additional exposure to radiation.

In a further variant the training data can first be emulated on the basis of pre-existing CTP data. After a first training phase using such emulated data, in a second training phase a fine adjustment to actual mCTA image datasets and matching noncontrast CT image datasets could take place. This is advantageous, since for a fine adjustment a significantly smaller amount of training data would have to be provided and thus the effort and an additional exposure to radiation is less in comparison to training directly on the basis of mCTA image datasets.

This means that in this variant emulated mCTA image datasets based on CTP image datasets are provided for the training as a training input dataset and likewise an emulated noncontrast image dataset based on CTP image datasets is provided as a training comparison dataset.

The emulated mCTA image datasets based on the CTP image datasets are based on the consideration that a subset of a time-resolved CTP image dataset, which is assigned to selected points in time, maps similar information to the at least three CT image datasets of an mCTA image dataset. This means that at least three image datasets of a CTP image dataset are specifically selected which substantially correspond to the mapped phases of an mCTA image dataset, whereas one of the first image datasets in time, in particular the first image dataset, of a CTP image dataset can be used as a training comparison dataset, in which generally as yet no influence of contrast agent in the imaging area of interest is present. Based on this image data, pretraining of the trained function can be performed in a first training phase.

A fine adjustment can then be made in a second training phase. Further training of the pretrained function takes place here on the basis of provided, measured mCTA image datasets as training input data and associated noncontrast CT image datasets as training comparison data. Advantageously, only a small amount of mCTA image data and associated noncontrast CT image datasets are necessary for a fine adjustment, wherein for most of the training use can be made of widely available, existing CTP image datasets.

In a further variant a fine adjustment such as this can where appropriate be bypassed if further steps are taken to support the transferability to mCTA image datasets. Such a step could consist of training the trained function so that it outputs the difference between the input and the desired output instead of the output itself (known as residual learning). This can advantageously not only reduce unwanted complexity in general, but in particular can prevent the trained function from also reproducing the look of perfusion image datasets in addition to removing the contrast agent contrast. This means that in this variant, training likewise takes place on the basis of emulated mCTA image datasets based on CTP image datasets and emulated noncontrast image datasets based on CTP image datasets, a method of residual learning being employed. Reference can be had here for example to Shen, Wei and Liu, Rujie "Learning Residual Images for Face Attribute Manipulation" (https://doi.org/10.48550/arxiv.1612.05363).

In all variants described here for the use of a trained function use can also be made, as an additional input dataset, of a native, noncontrast image dataset, as is normally present, as an auxiliary variable. Despite different scanning parameters compared to the mCTA image datasets, this provides additional complementary patient information, for example a better soft tissue contrast. This information can, as an additional input dataset in the trained function, result in a more accurate mapping by the trained function. If input such as this is provided, this must accordingly already be taken into account when training the trained function.

In the context of the invention, features which are described in respect of different forms of embodiments of the invention and/or different claim categories (method, use, apparatus, system, arrangement, etc.) can also be combined into further forms of embodiments of the invention. For example, a claim which relates to an apparatus can also be developed with features which are described or claimed in connection with a method, and vice versa. Functional features of a method can in this case be executed by correspondingly designed components in question.

The use of the indefinite article "a" or "an" does not rule out that the feature in question may also be present multiple times. The use of the expression "have" does not rule out that the terms linked via the expression "have" may be identical. For example, the computed tomography device has the computed tomography device. The use of the expression "unit" does not rule out that the object to which the expression "unit" relates may have multiple components that are spatially separated from one another.

The expression "on the basis of" can in the context of the present application in particular be understood in the sense of the expression "using". In particular, a wording, according which a first feature is generated on the basis of a second feature (alternatively: determined, ascertained, etc.), does not rule out that the first feature may be generated on the basis of a third feature (alternatively: determined, ascertained, etc.).

FIG. 1 shows a schematic operational sequence of a method for providing a virtual, noncontrast image dataset Dv,non of a patient 39 according to one or more example embodiments.

The method comprises the step of the provision S1 of a multiphase CT angiography image dataset of the patient 39 comprising at least three CT image datasets D1, D2, D3, that map an imaging area of the patient at three different points in time relative to an administration of contrast agent.

The method further comprises the step of the formation S2 of a minimum intensity image dataset Dmin of the imaging area on the basis of the at least three CT image datasets D1, D2, D3, wherein the image value of an image point of the minimum intensity image dataset Dmin is in each case based on the minimum value from among the image values of the image points, locally corresponding in the imaging area, in the at least three CT image datasets D1, D2, D3.

The method further comprises the step of the output S3 of the virtual, noncontrast image dataset Dv,non on the basis of the minimum intensity image dataset Dmin.

The imaging area of the patient 39, which is at least mapped by the at least three CT image datasets D1, D2, D3, just as by the virtual, noncontrast CT image dataset Dv,non and the minimum intensity image dataset Dmin, can comprise an anatomical and/or spatial area of the patient 39, which comprises a predetermined tissue area and/or a spatial area necessary for a diagnosis. Thus the imaging area in the case of a stroke patient in particular comprises the brain of the patient 39. In a different application the imaging area may also be different.

The acquisition areas of the respective image datasets may differ. When applying the method in the area of stroke diagnostic investigation, the acquisition area of the first CT image dataset D1 of the at least three CT image datasets D1, D2, D3 for example differs from an acquisition area of the second CT image dataset D2 and/or third CT image dataset D3 of the at least three CT image datasets D1, D2, D3 in particular in that the acquisition area of the first CT image dataset D1 at least comprises the patient 39 from the aortic arch to the crown, wherein the acquisition area of the second CT image dataset D2 and/or the acquisition area of the third CT image dataset D3 at least maps the patient 39 from the base of the skull to the crown.

In the case of different acquisition areas the method can in particular comprise restricting the CT image datasets to the desired imaging area of the virtual, noncontrast image dataset Dv,non when forming the minimum intensity image dataset Dmin.

If as described above the mCTA image dataset is provided such that the acquisition area of the first CT image dataset D1 at least comprises the patient 39 from the aortic arch to the crown, wherein the acquisition area of the second CT image dataset D2 and the acquisition area of the third CT image dataset D3 at least maps the patient 39 from the base of the skull to the crown, then for the formation of the minimum intensity image dataset Dmin a preliminary image dataset Dbase can be generated which is merely the size of the second and third CT image dataset. The minimum intensity image dataset can then be generated by populating the preliminary image dataset Dbase with respective image values determined by a minimum intensity projection on the basis of the mCTA image dataset and can be provided as a minimum intensity image dataset Dmin. This means the image values Vbase can substantially correspond to a min (V1,V2,V3), wherein the Vx image point values at corresponding positions in Dx where $x \in \{base,1,2,3\}$ correspond. Locally correspond means here that locally corresponding image points in the at least three CT image datasets D1, D2, D3 and accordingly also in the minimum intensity image dataset Dmin in each case map the same image area of the patient 39. This procedure applies similarly for other acquisition and imaging areas.

The at least three CT image datasets D1, D2, D3 each map the status of the distribution of contrast agent in the patient at different points in time relative to the administration of contrast agent.

In an advantageous method variant in this case the relative time interval between the first CT image dataset in time D1 and the second CT image dataset D2 of the at least three CT image datasets D1, D2, D3 or the relative time interval between the second CT image dataset in time D2 and the third CT image dataset D3 of the at least three CT image datasets D1, D2, D3 is at least 5 s. For the mCTA in connection with a diagnostic investigation in the context of a stroke a time interval of 7-10 s is particularly advantageous. In particular, the time delay between the respective starts of the data acquisition is selected such that the CT image datasets D1, D2, D3 are suitable for a subsequent diagnostic investigation. In contrast, a time difference between image datasets of a CTP is merely 1 to 2 s or less.

Since the at least three CT image datasets D1, D2, D3 represent the imaging area in each case at different points in time relative to the administration of contrast agent, it is assumed that for each mapped area or tissue type in the imaging area a mapping is present in one of the three CT image datasets D1, D2, D3 in which this is not influenced by contrast agent, so that the image area of the CT image dataset for which this applies can be used for this area as a noncontrast image. It can in this case then be further assumed that the respective minimum image value for a corresponding image point or voxel in the at least three CT image datasets D1, D2, D3, corresponds to the one which is not influenced by contrast agent, since the contrast agent would result in an increase in the image value relative to an initial value.

Thus a virtual, noncontrast CT image dataset is advantageously provided, which matches the provided mCTA image dataset.

Based on the provided multiphase CT angiography image dataset of the patient and the associated virtual, noncontrast image dataset Dv,non now provided, in further steps an improved perfusion image dataset can then be generated, in particular what are known as "perfusion maps", for example CBF or CBV.

Figure 2:
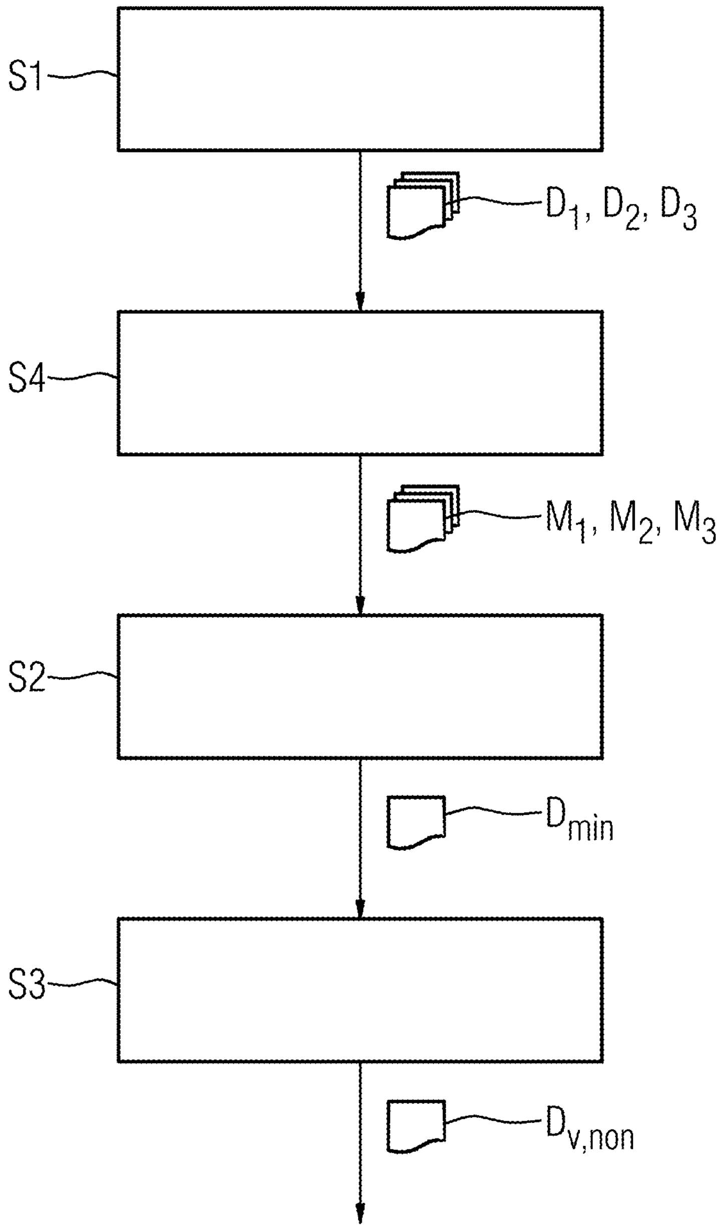
FIG. 2 shows a method for providing a virtual, noncontrast image dataset of a patient according to one or more example embodiments.

FIG. 2 shows a method for providing a virtual, noncontrast image dataset Dv,non of a patient 39 according to one or more example embodiments. S1, S2 and S3 can substantially correspond to the steps S1, S2 and S3 explained in the context of the description for FIG. 1.

However, this method variant further comprises the step of the performance S4 of a motion correction of the at least three CT image datasets D1, D2, D3, as a result of which motion-corrected CT image datasets M1, M2, M3 are provided. Based thereon, the minimum intensity image dataset Dmin is then formed in the subsequent step S2.

For a motion correction as can be employed in the context of the method there are various options that are known to the person skilled in the art from the prior art. Reference has already been made to examples in the general description. In particular, a known rigid registration of the at least three CT image datasets D1, D2, D3 can be used.

A motion correction can advantageously take into consideration movements of the patient 39 between the measured data acquisition for the at least three CT image datasets D1, D2, D3 and reduce the effect thereof, and thus an improved minimum intensity image dataset Dmin can be provided.

Figure 3:
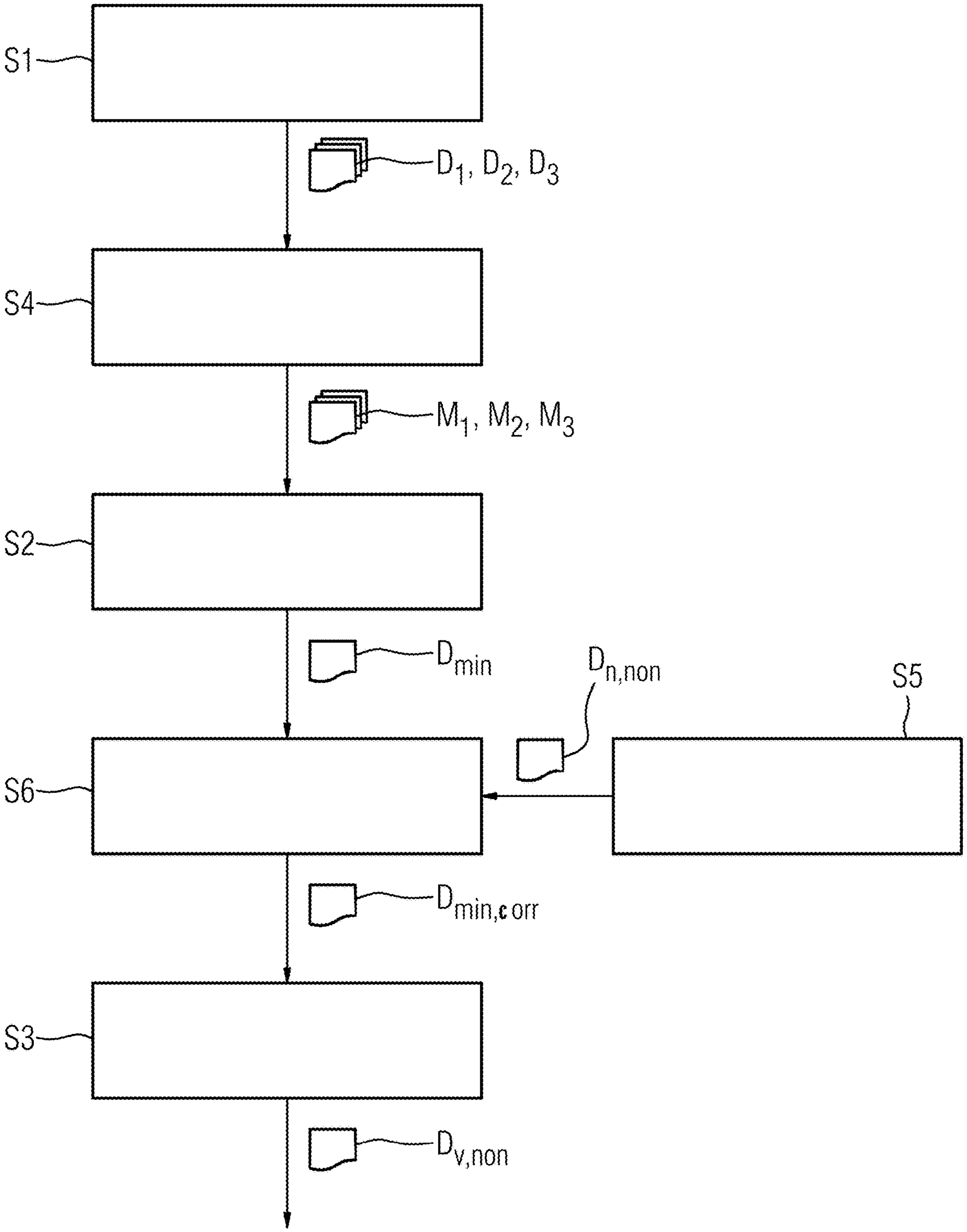
FIG. 3 shows a method for providing a virtual, noncontrast image dataset of a patient according to one or more example embodiments.

FIG. 3 shows a further variant of a method for providing a virtual, noncontrast image dataset Dv,non of a patient 39. In addition to the variant described in FIG. 2 this embodiment also comprises the step of the provision S5 of a native, noncontrast CT image dataset Dn,non that maps an imaging area of the patient 39 prior to administration of contrast agent and which was acquired with scanning parameters which differ from the scanning parameters of the mCTA image dataset. In a further step of the correction S6 the minimum intensity image dataset Dmin is corrected using the native, noncontrast CT image dataset Dn,non, as a result of which a corrected minimum intensity image dataset Dmin, corr is provided.

The virtual, noncontrast image dataset Dv,non to be output in the step of the output S5 is then based on the corrected minimum intensity image dataset Dmin, corr.

In this case too a motion correction can be performed prior to a comparison, in order to take account of possible movements of the patient between the acquisition of the native, noncontrast CT image dataset and the at least three CT image datasets D1, D2, D3 underlying the minimum intensity image dataset Dmin.

In this case the step of correction S6 can comprise ascertaining image areas in the minimum intensity image dataset Dmin that exceed a particular noise level value or that fall below a particular intensity value, and ascertaining at least one correction value on the basis of a comparison of the determined image areas with locally corresponding image areas in the native, noncontrast CT image dataset Dn,non. The at least one correction value is then applied to the noncorrected minimum intensity image dataset Dmin.

Likewise it is possible that, for the correction, image areas that exceed a particular noise level value or that fall below a particular intensity value are determined in at least one of the at least three CT image datasets D1, D2, D3, instead of in the minimum intensity image dataset Dmin, and on the basis of a comparison between image areas locally corresponding thereto in each case in the minimum intensity image dataset Dmin and in the native, noncontrast CT image dataset Dn,non at least one correction value for the determined image areas in the minimum intensity image dataset Dmin is ascertained.

Alternatively, the step of correction S6 can also comprise creating a perfusion image dataset on the basis of the at least three CT image datasets D1, D2, D3 of the mCTA image dataset of the patient 39, identifying image areas of the perfusion image dataset with locally increased contrast agent absorption, and ascertaining at least one correction value on the basis of a comparison between image areas locally corresponding thereto in the minimum intensity image dataset Dmin and locally corresponding image areas in the native, noncontrast CT image dataset Dn,non. The at least one correction value is then applied to the noncorrected minimum intensity image dataset.

Regardless of the execution, i.e. how the image areas are determined, the correction value can then be based in particular on a ratio of the image values in the determined image areas of the minimum intensity image dataset Dmin or of the native, noncontrast CT image dataset Dn,non to image values in a surrounding area of the determined image areas of the minimum intensity image dataset Dmin or of the native, noncontrast CT image dataset Dn,non. The comparison can in particular comprise comparing a contrast value between existing structures or image areas to surrounding structures or areas. If a ratio in both image datasets is similar or within a range of expectation, the probability is greater that no artifact is present here but that the image values are actually present as such. If the ratio differs significantly or lies outside expectations, the image values in the previously ascertained image areas of the minimum intensity image dataset Dmin are adjusted via at least one correction value, for example in a manner such that a ratio similar to or the same as the one in the native, noncontrast CT image dataset results therefrom or lies within the range of expectation.

Figure 4:
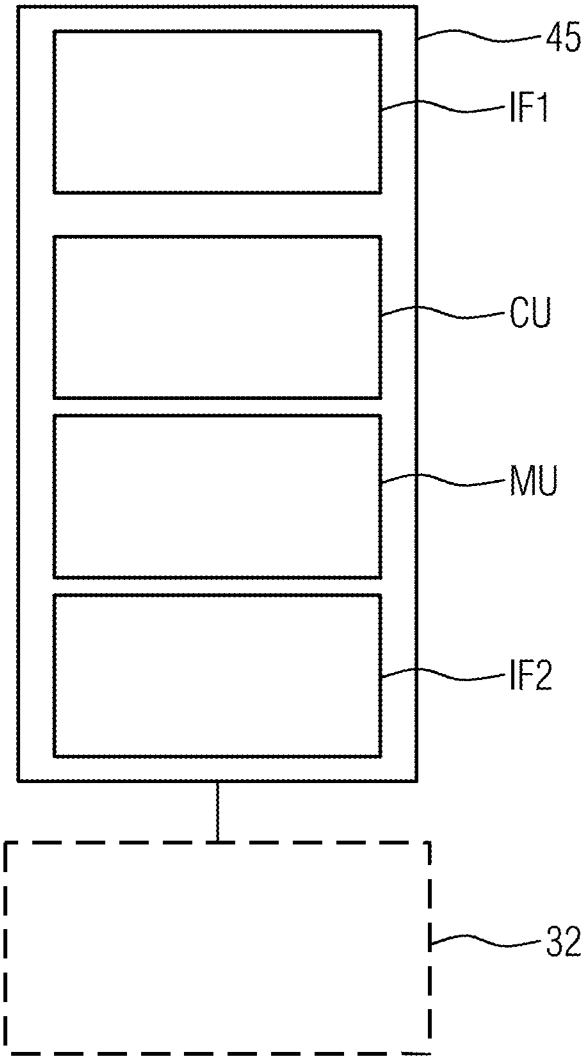
FIG. 4 shows an apparatus for providing a virtual, noncontrast image dataset of a patient according to one or more example embodiments.

FIG. 4 shows an apparatus 45 for providing a virtual, noncontrast image dataset Dv,non of a patient comprising

- a first interface IF1, designed to provide at least one multiphase CT image dataset of the patient, comprising at least three CT image datasets D1, D2, D3 that each map an imaging area of the patient at three different points in time relative to an administration of contrast agent,
- a computing unit CU, designed to form a minimum intensity image dataset Dmin of the imaging area on the basis of the at least three CT image datasets D1, D2, D3, wherein the image value of an image point of the minimum intensity image dataset Dmin is in each case based on the minimum value from among the image values of the image points, locally corresponding in the imaging area, in the at least three CT image datasets D1, D2, D3, and
- a second interface IF2, designed to output the virtual noncontrast image dataset Dv,non on the basis of the minimum intensity image dataset Dmin.

The apparatus 45 or the computing unit CU may in particular be a computer, a microcontroller or an integrated circuit. Alternatively, it may in this case be a real or virtual network of computers (a technical term for a real network is "cluster", a technical term for a virtual network is "cloud"). The apparatus can also be designed as a virtual system that is executed on a real computer or a real or virtual network of computers (virtualization).

An interface IF1, IF2 may be a hardware or software interface (for example PCI bus, USB or firewire). A computing unit may contain hardware elements or software elements, for example a microprocessor or what is known as an FPGA (the acronym stands for "Field Programmable Gate Array").

The interfaces IF1, IF2 can in particular comprise multiple subsidiary interfaces. In other words, the interfaces IF1, IF2 can also comprise a plurality of interfaces. The computing unit can in particular comprise multiple subsidiary computing units that execute different steps of the respective methods. In other words, the computing unit can also be understood as a plurality of computing units.

The apparatus 45 can additionally also comprise a memory unit. A memory unit can be implemented as a nonpermanent working memory (Random Access Memory, RAM for short) or as a permanent mass memory (hard disk, USB stick, SD card, solid state disk).

Such an apparatus 45 for providing a virtual, noncontrast image dataset Dv,non of a patient 39 can in particular be designed to execute the previously described inventive methods for providing a virtual, noncontrast image dataset Dv,non of a patient 39 and aspects thereof. The apparatus 45 can be designed to execute the methods and aspects thereof, in that the interfaces IF1, IF2 and the computing unit CU are designed to execute the corresponding method steps.

The apparatus can further be connected to a CT device 32 which is designed to acquire measured data for an mCTA image dataset.

Figure 5:
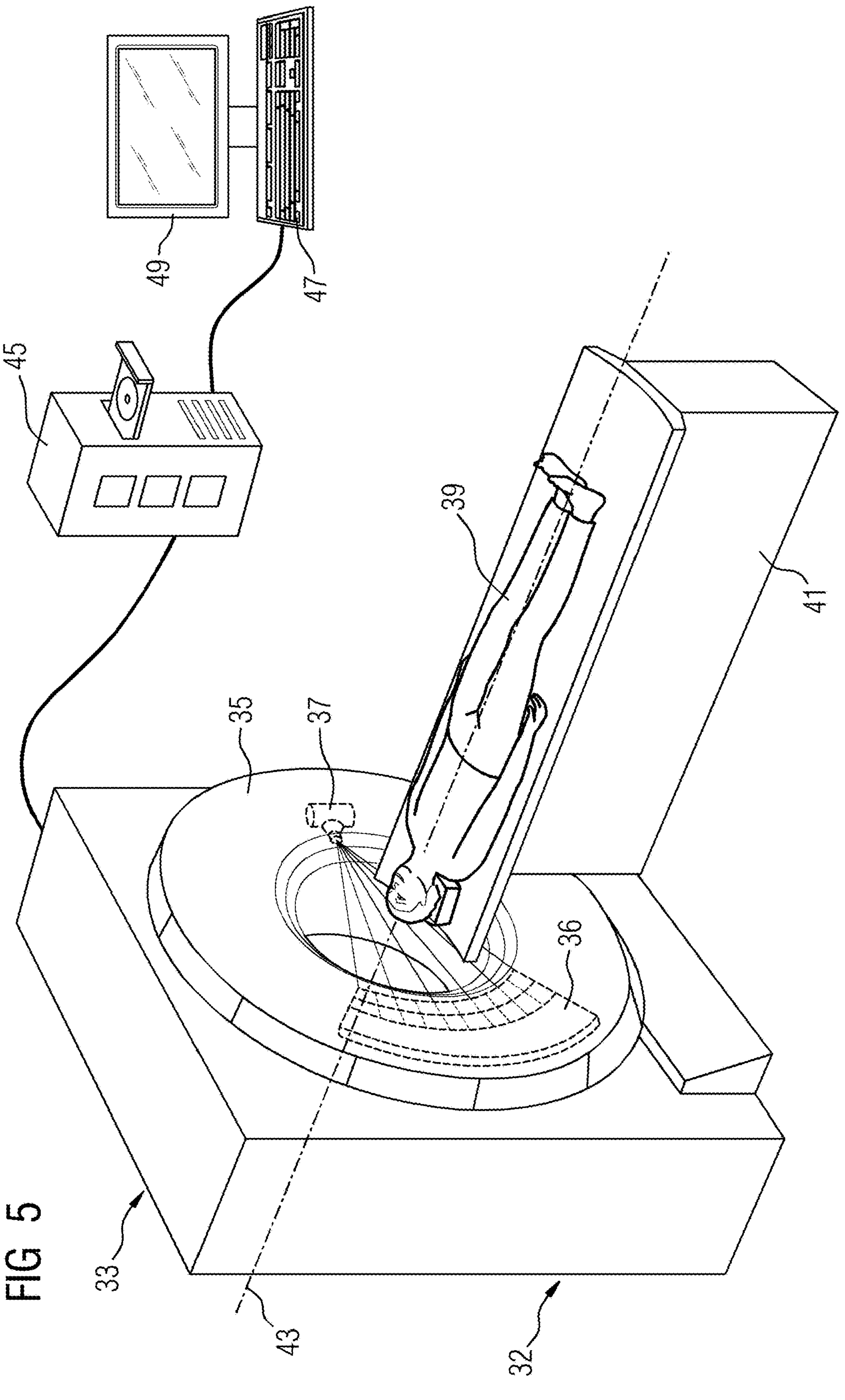
FIG. 5 shows a computed tomography device having an apparatus for providing a virtual, noncontrast image dataset of a patient according to one or more example embodiments.

FIG. 5 shows an inventive CT device 32. The CT device has a gantry 33 with a rotor 35. The rotor 35 comprises at least one X-ray source 37, in particular an X-ray tube, and opposite thereto at least one X-ray detector 2. The X-ray detector 2 and the radiation source 37 can be rotated about a common axis 43 (also called an axis of rotation). The patient 39 is mounted on a patient couch 41 and can be moved along the axis of rotation 43 through the gantry 33. In general the patient 39 may for example comprise an animal patient and/or a human patient.

Measured data is normally acquired in the form of a plurality of (raw) projection datasets of the patient 39 from a plurality of projection angles during a relative rotary motion between the X-ray source 37 and the patient 39, while the patient 39 is moved continually or sequentially through the gantry 33 via the patient couch 41. Then on the basis of the projection datasets an image dataset of the imaging areas can be reconstructed via a mathematical method, for example comprising a filtered backprojection or an iterative reconstruction method.

The CT device 32 comprises a computer system 45. The computer system 45 can also comprise a reconstruction unit for reconstructing image datasets on the basis of the measured data determined by the imaging device 32. The computer system 45 can also have a control unit for actuating the CT device. The computer system 45 in particular comprises an apparatus 45 for providing a virtual, noncontrast CT image dataset.

The apparatus 45, comprised by the computer system 45, for providing a virtual, noncontrast image dataset Dv,non of a patient is in particular designed to perform an inventive method for generating a results image dataset as described previously.

Furthermore, an input device 47 and an output device 49 are connected to the computer system 45. The input device 47 and the output device 49 may for example enable an interaction, for example a manual configuration, a confirmation or an actuation of a method step by a user. For example, the at least three CT image datasets, the minimum intensity image dataset or the virtual, noncontrast CT image dataset can be displayed to the user on the output apparatus 49 comprising a monitor.

Although the present invention has been disclosed in the form of preferred embodiments and variations thereon, it will be understood that numerous additional modifications and variations could be made thereto without departing from the scope of the invention. For the sake of clarity, it is to be understood that the use of "a" or "an" throughout this application does not exclude a plurality, and "comprising" does not exclude other steps or elements. The expression "a number of" means "at least one". The mention of a "unit" or a "device" does not preclude the use of more than one unit or device. The expression "a number of" has to be understood as "at least one".

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "on," "connected," "engaged," "interfaced," and "coupled." Unless explicitly described as being "direct," when a relationship between first and second elements is described in the disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" on, connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

It is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed above. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments. The present invention may, however, be embodied in many alternate forms and should not be construed as limited to only the embodiments set forth herein.

In addition, or alternative, to that discussed above, units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above.

Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one example embodiment relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

The invention claimed is:

1. A method for providing a virtual, noncontrast image dataset of a patient, the method comprising:

providing a multiphase computed tomography (CT) angiography image dataset of the patient, the multiphase CT angiography image dataset comprising at least three CT image datasets that map an imaging area of the patient at three different points in time relative to an administration of a contrast agent;

forming a minimum intensity image dataset of the imaging area based on the at least three CT image datasets, an image value of an image point of the minimum intensity image dataset is in each case based on a minimum value from among image values of the image point, locally corresponding in the imaging area, in the at least three CT image datasets; and outputting of the virtual, noncontrast image dataset based on the minimum intensity image dataset.

2. The method of claim 1, wherein a relative time interval between a first CT image dataset and a second CT image dataset of the at least three CT image datasets or a relative time interval between the second CT image dataset and a third CT image dataset of the at least three CT image datasets is at least 5 s.

3. The method of claim 2, wherein the imaging area comprises a brain of the patient.

4. The method of claim 3, wherein an acquisition area of a first CT image dataset of the at least three CT image datasets differs from at least one of an acquisition area of a second CT image dataset of the at least three CT image datasets or an acquisition area of a third CT image dataset of the at least three CT image datasets.

5. The method of claim 4, wherein the acquisition area of the first CT image dataset at least comprises the patient from an aortic arch to a crown, and wherein at least one of the acquisition area of the second CT image dataset or the acquisition area of the third CT image dataset at least maps the patient from a base of a skull to the crown.

6. The method of claim 5, further comprising: performing a motion correction of the at least three CT image datasets to create motion-corrected CT image datasets, wherein the forming forms the minimum intensity image dataset based on the motion-corrected CT image datasets.

7. The method of claim 6, further comprising: providing a native, noncontrast CT image dataset that maps an imaging area of the patient prior to the administration of the contrast agent; and correcting the minimum intensity image dataset using the native, noncontrast CT image dataset, wherein the outputting outputs the virtual, noncontrast image dataset based on the corrected minimum intensity image dataset.

8. The method of claim 1, wherein the imaging area comprises a brain of the patient.

9. The method of claim 1, wherein an acquisition area of a first CT image dataset of the at least three CT image datasets differs from at least one of an acquisition area of a second CT image dataset of the at least three CT image datasets or an acquisition area of a third CT image dataset of the at least three CT image datasets.

10. The method of claim 9, wherein the acquisition area of the first CT image dataset at least comprises the patient from an aortic arch to a crown, and wherein at least one of the acquisition area of the second CT image dataset or the acquisition area of the third CT image dataset at least maps the patient from a base of a skull to the crown.

11. The method of claim 1, further comprising: performing a motion correction of the at least three CT image datasets to create motion-corrected CT image datasets, wherein the forming forms the minimum intensity image dataset based on the motion-corrected CT image datasets.

12. The method of claim 1, further comprising: providing a native, noncontrast CT image dataset that maps an imaging area of the patient prior to the administration of the contrast agent; and correcting the minimum intensity image dataset using the native, noncontrast CT image dataset, wherein the outputting outputs the virtual, noncontrast image dataset based on the corrected minimum intensity image dataset.

13. The method of claim 12, wherein the correcting comprises: ascertaining image areas in the minimum intensity image dataset or in at least one of the at least three CT image datasets, that exceed a particular noise level value or that fall below a particular intensity value, and ascertaining a correction value based on a comparison between image areas in each case locally corresponding in the minimum intensity image dataset and in the native, noncontrast CT image dataset.

14. The method of claim 13, wherein the correction value is based on a ratio of the image values in the ascertained image areas of the minimum intensity image dataset or of the native, noncontrast CT image dataset to image values in a surrounding area of the ascertained image areas of the minimum intensity image dataset or of the native, noncontrast CT image dataset.

15. The method of claim 12, wherein the correcting comprises: creating a perfusion image dataset based on the at least three CT image datasets of the multiphase CT angiography image dataset of the patient, identifying image areas of the perfusion image dataset with locally increased contrast agent absorption, and ascertaining a correction value based on a comparison between image areas locally corresponding in the minimum intensity image dataset and in the native, noncontrast CT image dataset.

16. A method for providing a perfusion image dataset, wherein providing the multiphase CT angiography image dataset of the patient comprising at least three CT image datasets that map the imaging area of the patient at three different points in time relative to the administration of the contrast agent; providing the virtual, noncontrast CT image dataset in accordance with the method of claim 1; and generating and providing the perfusion image dataset based on the at least three CT image datasets and the virtual, noncontrast CT image dataset.

17. A non-transitory computer-readable storage medium, on which are stored program sections that, when executed by an apparatus for providing a virtual, noncontrast image dataset of a patient, causes the apparatus to perform the method of claim 1.

18. An apparatus for providing a virtual, noncontrast image dataset of a patient, the apparatus comprising: a first interface configured to provide at least one multiphase computed tomography (CT) image dataset of the patient, the at least one multiphase CT image dataset comprising at least three CT image datasets that map an imaging area of the patient at three different points in time relative to an administration of contrast agent; a computing unit configured to form a minimum intensity image dataset of the imaging area based on the at least three CT image datasets, an image value of an image point of the minimum intensity image dataset is in each case based on a minimum value from among the image values of the image points, locally corresponding in the imaging area, in the at least three CT image datasets; and a second interface configured to output the virtual, noncontrast image dataset based on the minimum intensity image dataset.

19. A computed tomography device comprising the apparatus of claim 18.

* * * * *